(12) United States Patent
Mouritzen et al.

(10) Patent No.: US 8,961,950 B2
(45) Date of Patent: Feb. 24, 2015

(54) NEOADJUVANT TREATMENT OF CANCER WITH PROLEUKIN

(76) Inventors: Ulrik Mouritzen, Rungsted Kyst (DK); Christiane Voit, Berlin (DE)

( * ) Notice: Subject to any disclaimer, the term of this patent is extended or adjusted under 35 U.S.C. 154(b) by 0 days.

(21) Appl. No.: 13/816,426

(22) PCT Filed: Aug. 10, 2011

(86) PCT No.: PCT/US2011/047239
§ 371 (c)(1),
(2), (4) Date: Feb. 26, 2013

(87) PCT Pub. No.: WO2012/021609
PCT Pub. Date: Feb. 16, 2012

(65) Prior Publication Data
US 2013/0156730 A1    Jun. 20, 2013

Related U.S. Application Data

(60) Provisional application No. 61/373,074, filed on Aug. 12, 2010.

(51) Int. Cl.
*A61K 38/20* (2006.01)
*G01N 33/50* (2006.01)

(52) U.S. Cl.
CPC ........ *A61K 38/2013* (2013.01); *G01N 33/5011* (2013.01); *G01N 2333/55* (2013.01)
USPC ...................................... 424/85.2

(58) Field of Classification Search
CPC .................................. A61K 38/2013
USPC ...................................... 424/85.2
See application file for complete search history.

(56) References Cited

U.S. PATENT DOCUMENTS

2005/0163749 A1    7/2005   Talor
2010/0047205 A1    2/2010   Hadden et al.

FOREIGN PATENT DOCUMENTS

WO    WO 2012/021609 A2    2/2012

OTHER PUBLICATIONS

International Search Report issued in corresponding application PCT/US2011/047239, dated Apr. 3, 2012.
Whiteside et al. "Evidence for Local and Systemic Activation of Immune Cells by Peritumoral Injections of Interleukin 2 in Patients with Advanced Squamous Cell Carcinoma of the Head and Neck." Cancer Res. Dec. 1, 1993, vol. 53, No. 23, pp. 5654-5662; abstract; Table 2-4; pg. 5655, para 2-3.
Foureau et al. "Skin Tumor Responsiveness to IL-2 Treatment Correlates to CD8 Treg Expansion in an Immunocompetent Mouse Model." J. Immunol. Apr. 2010, vol. 184, Meeting Abstract Suppl., Abstract No. 100.15.
Balch et al. "Final version of 2009 AJCC melanoma staging and classification." J. Clin. Oncol. Dec. 20, 2009, vol. 27, No. 36, pp. 6199-6206; abstract; p. 6200, para 1-2.
Cortesina et al. "Interleukin-2 Injected around Tumor-Draining Lymph Nodes in Head and Neck Cancer." Head Neck. Mar.-Apr. 1991, vol. 13, No. 2, pp. 125-131.

*Primary Examiner* — Prema Mertz
(74) *Attorney, Agent, or Firm* — Davidson, Davidson & Kappel, LLC

(57) ABSTRACT

Low doses of IL-2 are administered locally and neo-adjuvantly to patients with early stages of the disease. This will result in local high concentrations of IL-2 within the relevant tumor draining lymph nodes. Patients with only early stages of disease will be more responsive to immunotherapy with the expectation of improved survival of patients compared to current therapy standards.

11 Claims, 4 Drawing Sheets

NEOADJUVANT TREATMENT OF CANCER WITH PROLEUKIN

This application is a national phase under 35 U.S.C. §371 of International Application No. PCT/US11/47239, filed on Aug. 10, 2011 (which was published as WO 2012/021609, on Feb. 16, 2012), which claims priority U.S. Provisional Application 61/373,074, filed on Aug. 12, 2010, the disclosures of which are all hereby incorporated by reference herein.

Throughout this application various publications are referenced. The disclosures of these publications are hereby incorporated by reference in their entirety into this application in order to more fully describe the state of the art to which the invention pertains.

FIELD OF INVENTION

Neo-adjuvant treatment of cancer using local administration of cytokines, in particular IL-2.

BACKGROUND

The incidence of melanoma is approximately 60.000 per year in the US. Approximately 10% of patients will present with high risk stage II disease (10 year survival of app. 55%) [Balch C M, Buzaid A C, Soong S J et al. *Final version of the American Joint Committee on Cancer staging system for cutaneous melanoma*. J Clin Oncol 2001; 19(16):3635-3648] and approximately 20% of patients with any stage II or III. For patients with stage II and III melanoma survival rates are not satisfactory with currently available treatment options.

Proleukin® is the brand name for a prescription form of recombinant human interleukin-2 (rhIL-2). It is labeled for treatment of adults with metastatic melanoma and metastatic kidney cancer. Proleukin® has been used for over 15 years in the treatment of metastatic melanoma and metastatic kidney cancer (renal cell carcinoma). Interleukin-2 was first approved by the FDA for treatment of stage IV melanoma and renal cell carcinoma in 1992. The use of interleukin-2 has been extensively studied in patients with unresectable AJCC [The American Joint Committee on Cancer "AJCC"] stage III and stage IV melanoma with infrequent but sometimes impressive clinical results.

Experiences gained from the use of Interleukin-2 in patients with stage IV renal cell carcinoma, stage IV malignant melanoma and unresectable stage III malignant melanoma demonstrates that Interleukin-2 has therapeutic potential in these patient groups. The frequency of clinical responses is however limited with objective response rates of up to 20% and with approximately 5% of patients achieving complete responses. Atkins M B, Lotze M T, Dutcher J P et al., *High-dose recombinant interleukin 2 therapy for patients with metastatic melanoma: analysis of 270 patients treated between 1985 and 1993*, J Clin Oncol 1999; 17(7):2105-2116; Rosenberg S A, Yang J C, White D E, Steinberg S M., *Durability of complete responses in patients with metastatic cancer treated with high-dose interleukin-2: identification of the antigens mediating response*, Ann Surg 1998; 228(3):307-319.8, 9. In patients where complete responses are obtained, these responses have frequently shown to be durable with duration of responses exceeding 10 years. Rosenberg S A, Yang J C, White D E, Steinberg S M., Durability of complete responses in patients with metastatic cancer treated with high-dose interleukin-2: identification of the antigens mediating response, Ann Surg 1998; 228(3):307-319. High dose IL-2 treatment, however, is associated with substantial toxicities, which has limited its clinical use. For example, high dose bolus interleukin 2 (IL-2) used in the treatment of metastatic melanoma and renal cell carcinoma is known to cause vascular leak syndrome and serious cardiac toxicities, including myocarditis in a significant fraction of the patients.

Only a limited number of publications contemplate potential neoadjuvant application of cytokines for the treatment of Stage II and III melanoma. For example, Granolucyte Macrophage Stimulating Factor (GM-CSF) has been administered neoadjuvantly to patients with stage I melanoma in order to examine responsive effects on dendritic cells and T-cell responses. See Vuylsteke R J C L, Molenkamp B G, Gietema H A et al., *Local administration of granulocyte/macrophage colony-stimulating factor increases the number and activation state of dendritic cells in the sentinel lymph node of early-stage melanoma*, Cancer Res 2004; 64(22): 8456-8460; Molenkamp B G, Vuylsteke R J C L, van Leeuwen P A M et al., *Matched skin and sentinel lymph node samples of melanoma patients reveal exclusive migration of mature dendritic cells*, AM J PATHOL 2005; 167(5):1301-1307.; Vuylsteke R J C L, Molenkamp B G, van Leeuwen P A M et al. *Tumor-specific CD8+ T cell reactivity in the sentinel lymph node of GM-CSF-treated stage I melanoma patients is associated with high myeloid dendritic cell content*, Clin Cancer Res 2006; 12(9):2826-2833. However, direct assessment of anti-tumor effects within the lymph nodes following local neo-adjuvant administration of immuno-modulatory compounds have not been performed (to our knowledge). Toll like receptor-9 (CpG-7909/PF-3512676) has also been explored using local administration with clear biological effects observed within the draining lymph nodes. Molenkamp B G, Sluijter B J, van Leeuwen P A et al., *Local Administration of PF-3512676 CpG-B Instigates Tumor-Specific CD8+ T-Cell Reactivity in Melanoma Patients*, Clinical cancer research: an official journal of the American Association for Cancer Research, 2008; 14(14):4532-4542; Sluijter B, Molenkamp B, deGruijl T et al. *The effects of pre-operative administration of CpG 7909 on dendritic and T cell subsets in the sentinel lymph node of stage I/II melanoma patients*, Melanoma research 16, suppl. 1, S43-S44. 2006 (Abstract). Direct assessment of anti-tumor effects within the tumor-draining lymph nodes following local administration of immuno-modulatory agents has not been explored in a neo-adjuvant setting in patients with stage A clinical trial in patients with stage is currently ongoing with patients receiving a vaccination with melanoma antigen peptides in combination with low doses of IL-2 (Clinical trials.gov; NCT00112242). This trial is however not designed to inject IL-2 in the tumor draining lymph nodes. Interleukin-2 has been administered intra-lesionally in patients with stage IV disease and a local high response rate was observed. Radny P, Caroli U M, Bauer J et al., *Phase II trial of intralesional therapy with interleukin-2 in soft-tissue melanoma metastases*. Br J Cancer 2003; 89(9):1620-1626. However this trial was undertaken in patients with advanced disease and consequently limited systemic responses were observed.

U.S. 2002146397A is purportedly directed to vaccine immunotherapy for immune suppressed patients purportedly teaches a method treating cancer and other persistent lesions includes the steps of administering an effective amount of a natural cytokine mixture as an adjuvant to endogenous or exogenous administered antigen to the cancer or other persistent lesions.

U.S. 2009220472A is purportedly directed to a method comprising identification of tumor-reactive T-lymphocytes from a patients sentinel and/or metinel lymph nodes draining a malignant melanoma or a metastasis there from, resection of the one or more nodes and, optionally all or part of the tumor or metastasis, isolation of tumor-reactive T-lymphocytes from said lymph nodes, in vitro expansion of said tumor-reactive T-lymphocytes, and administration of the thus obtained tumor-reactive T-lymphocytes to the patient, wherein the T-lymphocytes are CD4+ helper and/or CD8+ T-lymphocytes purportedly has therapeutic potential.

U.S. 2009297489A is purportedly directed to a method for expansion and activation of tumor-reactive lymphocytes, in particular CD4+ helper and/or CD8+ T-lymphocytes, which may be used for treating and/or preventing cancer. The method purportedly comprises a first phase of stimulating tumor-reactive CD4+ T helper and/or CD8+ T-lymphocytes with tumor-derived antigen together with at least one substance having agonistic activity towards the IL-2 receptor to promote survival of tumor-reactive CD4+ T helper and/or CD8+ T-lymphocytes; and a second phase of activating and promoting growth of tumor-reactive CD4+ T helper and/or CD8+ T-lymphocytes, wherein the second phase is initiated when the CD25 cell surface marker (or IL-2R marker) is down-regulated on CD4+ T helper and/or CD8+ T-lymphocytes.

U.S. 2003180254A is purportedly directed to a method for activating a mammalian immune system entailing a series of IL-2 administrations that are effected intermittently over an extended period. Each administration of IL-2 is purportedly sufficient to allow spontaneous DNA synthesis in peripheral blood or lymph node cells of the patient to increase and peak, and each subsequent administration follows the preceding administration in the series by a period of time that is sufficient to allow IL-2 receptor expression in peripheral or lymph node blood of the patient to increase, peak and then decrease to 50 percent of peak value.

Arora A, Su G, Mathiowitz E, Reineke J, Chang A E, Sabel M S., *Neoadjuvant intratumoral cytokine-loaded microspheres are superior to postoperative autologous cellular vaccines in generating systemic anti-tumor immunity*, J Surg Oncol. 2006 Oct. 1; 94(5):403-12 discusses a treatment of intratumoral IL-12 and TNF-alpha loaded PLAM which purportedly led to both local eradication of tumor and the induction of specific anti-tumor T-cells in the lymph nodes and spleens, resulting in memory immune response. Neoadjuvant treatment was said to be significantly superior to postoperative autologous cellular vaccines using IL-12 and TNF-alpha PLAM.

SUMMARY OF THE INVENTION

Most clinical trials assessing the therapeutic effect of novel immunotherapies within melanoma have been applied in patients with stage IV disease. This may, in part, explain why most of the clinical trials applying different immunotherapeutic approaches such as therapies with recombinant cytokines, vaccinations and adoptive cell transfer in the last 20 years have resulted in insufficient or suboptimal objective response rates. As the tumor cell mass in patients with stage IV melanoma has undergone a process of clonal diversification and selection pressure by the immune system, the tumor cells have developed multiple defensive mechanisms to evade an immune attack. Kirkwood J M, Tarhini A A, Panelli M C, Moschos S J, Zarour H M, Butterfield L H, Gogas H J. Next generation of immunotherapy for melanoma. J Clin Oncol 2008 Jul. 10; 26(20):3445-55; Zou W. Immunosuppressive networks in the tumour environment and their therapeutic relevance. Nat Rev Cancer 2005 April; 5(4):263-74.

Malignant melanoma, as an indication for testing immunotherapeutic interventions, is however relevant, as the tumors have been shown to be relatively immunogenic.

The presence of malignant cells in the sentinel lymph nodes (SLN) can be identified and verified in vivo by high-resolution ultrasonography (US) and fine needle aspiration cytology (FNAC) Voit C, Kron M, Schafer G, Schoengen A, Audring H, Lukowsky A, Schwurzer-Voit M, Sterry W, Winter H, Rademaker J. *Ultrasound-guided Fine Needle Aspiration Cytology prior to Sentinel Lymph Node Biopsy in Melanoma Patients*. Ann Surg Oncol 2006 December; 13(12): 1682-9; Schafer-Hesterberg G, Schoengen A, Sterry W, Voit C. *Use of ultrasound to early identify, diagnose and localize metastases in melanoma patients*. Expert Rev Anticancer Ther 2007 December; 7(12):1707-16. The presence of malignant cells within the SLN as identified by US-guided FNAC has been shown to be highly predictive of a positive SLN biopsy when subjects subsequently underwent surgical removal of the SLN Voit C, Kron M, Schafer G, Schoengen A, Audring H, Lukowsky A, Schwurzer-Voit M, Sterry W, Winter H, Rademaker J. *Ultrasound-guided Fine Needle Aspiration Cytology prior to Sentinel Lymph Node Biopsy in Melanoma Patients*. Ann Surg Oncol 2006 December; 13(12): 1682-9; Voit C A, van Akkooi A C, Schafer-Hesterberg G, Schoengen A, Schmitz P I, Sterry W, Eggermont A M. *Rotterdam Criteria for sentinel node (SN) tumor burden and the accuracy of ultrasound (US)-guided fine-needle aspiration cytology (FNAC): can US-guided FNAC replace SN staging in patients with melanoma?* J Clin Oncol 2009 Oct. 20; 27(30):4994-5000; Voit C A, Schafer-Hesterberg G, Kron M, van Akkooi A C, Rademaker J, Lukowsky A, Schoengen A, Schwurzer-Voit M, Sterry W, Krause M, Rowert-Huber J, Eggermont A M. *Impact of molecular staging methods in primary melanoma: reverse-transcriptase polymerase chain reaction (RT-PCR) of ultrasound-guided aspirate of the sentinel node does not improve diagnostic accuracy, but RT-PCR of peripheral blood does predict survival*. J Clin Oncol 2008 Dec. 10; 26(35):5742-7. (Voit et al., Ultrasound (US) Morphology Criteria Predict Metastatic Disease of the Sentinel Nodes (SN) in Melanoma Patients, J Clin Oncol, 2010; 28: 847-52).

This technique allows for testing for anti-tumor activity in a clinical setting of relatively low tumor burden.

Recombinant interleukin-2 (IL-2) has therapeutic potential in patients with malignant melanoma stage I, II and III, if administered subcutaneously (s.c.) and locally at the site of the primary melanoma lesion as a neo-adjuvant treatment. If applied prior to the standard diagnostic sentinel lymph node biopsy (SLNB) or complete lymph node dissection (cLND), the prognosis for the patients may be improved as compared to surgical intervention alone.

When recombinant intereukin-2 is administered s.c. and locally at the site of the primary melanoma lesion, a fraction of the cytokine will drain via the lymphatic vessels to the draining lymph nodes allowing local high concentrations within the tumor draining lymph nodes. Within the draining lymph nodes, the normal immune response towards malignant cells has been suppressed by the presence of the primary lesion and potential metastatic seed within the draining lymph nodes. A local high concentration of IL-2 within the draining lymph nodes, optimally combined with removal of the primary lesion, may revert the tumor induced tolerance towards the malignant cells within the sentinel nodes and potentially also boost an antigen specific immune response towards distant metastatic seed. This may result in improved survival for the patients compared to surgery alone, which is the standard therapy today.

The ideal therapeutic setting would be to treat high risk early stage melanoma, Stage I (eg. T1b: lesions with ulceration and/or Clark level IV-V according to AJCC 2006) or stage II melanoma. Optimally, the primary lesion will be removed prior to or close to the initiation of local neo-adjuvant treatment with IL-2 at a relatively low dose level (about 100 ng to about 1000 ng, although higher doses would also be effective). An intermittent dosing schedule (eg. thrice weekly) and of about 4 weeks duration would be considered of appropriate to stimulate an immune response within the tumor draining lymph nodes. Following the neo-adjuvant treatment period, surgical removal of the sentinel nodes, as identified by lymphatic mapping, would serve the purpose of removing any residual tumor cells left within the lymph nodes while the tumor reactive T-cells and B-cells would remain in the body and fight any distant metastatic seeds. The combination of the above described elements in treating early stages of melanoma has not been described previously and the above described elements should ideally be combined to maximize the therapeutic benefit for patients.

Other cytokines/immuno-modulators may have similar therapeutic potential, if applied locally targeting immunomodulatory relevant concentrations within the tumor draining lymph nodes.

It is an object of the present invention to develop local cytokine application (IL-2) to provide clinical benefit to patients with early stage malignant melanoma (e.g. high risk stage I and high risk stage II malignant melanoma). Patients with stage III melanoma will also have therapeutic benefit of local neo-adjuvant treatment with IL-2 prior to removal of the lymph nodes.

It is a further object to provide a method for treating cancer, comprising the neo-adjuvant administration to a patient of a dose of from about 10 ng to about 200 μg/ml of IL-2 locally in the area of the primary tumor with the objective of stimulating the tumor draining lymph nodes before surgically removal of the lymph nodes in order to stimulate an immune response towards the cancer cells.

It is another object of the present invention to provide a method for testing the anti-tumor activity of immunomodulatory agents in a patient having metastatic cancer cells seeded into the lymph nodes comprising the conduct of ultrasound guided fine-needle aspiration cytology for the verification of the presence of malignant cells, the injection of one or more doses of the immunomodulatory agent in the vicinity of the tumor, such that the immunomodulatory agent drains to the tumor draining lymph nodes, including the sentinel lymph node(s) and stimulates an immune response. Subsequent removal of the tumor draining lymph nodes of the patient will allow for direct assessment of anti-tumor activity by examining the tissue specimens for the presence of malignant cells.

It is also an object of the present invention to provide a method of neo-adjuvant treatment of a patient having other solid cancers than melanoma by administering IL-2 in the area of a tumor (which may already have been removed), such that the IL-2 drains to the tumor draining lymph nodes, including a sentinel lymph node, wherein the administered dose is from about 10 ng to about 200 μg, administered over an approximate 4 week time period as a neo-adjuvant treatment. Lymph nodes may subsequently be removed for diagnostic purposes and to remove any remaining cancer cells within the lymph nodes of the patient.

DETAILED DESCRIPTION OF THE INVENTION

All scientific and technical terms used in this application have meanings commonly used in the art unless otherwise specified.

Cytokines like IL-2 are used within the normal human body to provide local signals between cells in order to orchestrate and adequate immune response towards pathogens and cancer cells. IL-2, and other cytokines should therefore ideally be used locally in a microenvironment in order to effectively manipulate an immune response with limited side effects.

Survival for patients having early stage cancer, such as melanoma, may be improved with relevant immunotherapeutic intervention, if it is applied prior to surgical intervention, leaving the anatomical structure and function of the lymph nodes intact. Removal of the primary lesion before immunotherapeutic intervention may however reduce local immunosuppressive signals to the tumor draining lymph nodes and may improve therapeutic outcome. Patients with earlier stages of disease or disease still confined to the sentinel lymph nodes (SLN) may be more responsive to cytokine based immunotherapy. A recent study reported by Kirkwood et Al. supports that patients with stage IIIb melanoma may be more likely to respond to immunotherapies as compared to patients with stage IV disease. Moschos S J, Edington H D, Land S R et al., *Neoadjuvant treatment of regional stage IIIB melanoma with high-dose interferon alfa-2b induces objective tumor regression in association with modulation of tumor infiltrating host cellular immune responses*, Journal of Clinical Oncology: Official Journal of the American Society of Clinical Oncology 2006; 24(19):3164-3171; Chang E, Rosenberg S A., *Patients with melanoma metastases at cutaneous and subcutaneous sites are highly susceptible to interleukin-2-based therapy*, J IMMUNOTHER 2001; 24(1):88-90.

Local immune suppression is an active process induced by the malignant cells within the tumour microenvironment and within the sentinel lymph nodes (SLN). Gajewski T F, Meng Y, Harlin H., *Immune suppression in the tumor microenvironment. J Immunother*, 2006; 29(3):233-240; Zou W., *Immunosuppressive networks in the tumour environment and their therapeutic relevance*, NAT REV CANCER 2005; 5(4):263-274. T-cell receptor zeta subunit (TCR) is downregulated and Indoleamine 2,3-dioxygenase (IDO) is upregulated within the tumour draining lymph nodes as part of the elements involved in this regional immune suppression (Abstract 8000, BP Negin, ASCO 2006).

Local immune suppression may to some extent be reverted by IL-2 administered at relatively high local concentrations as observed by the experimental use of IL-2 administered intralesional in cutaneous and soft tissue lesions in patients with stage IV disease. Radny P, Caroli U M, Bauer J et al., *Phase II trial of intralesional therapy with interleukin-2 in soft-tissue melanoma metastases*, Br J Cancer 2003; 89(9): 1620-1626. According to the Radny article, although systemic responses have been rare, and thereby the overall therapeutic benefit limited, local responses were frequently observed. Patients with stage IV disease are however not ideal for such treatment as the malignant cells have clearly escaped the immune system and the malignant cells have developed multiple mechanisms for evading immune attack.

The present invention provides a solution to this problem by providing local immune activation within the sentinel lymph node leading to anti-tumor activity by relevant local cytokine application. For example, recombinant interleukin-2 (IL-2) has therapeutic potential in patients with early stages (high risk stage I-II) of malignant melanoma, if administered subcutaneously (s.c.) and locally at the site of the primary melanoma lesion. By the same immunomodulatory mechanisms, IL-2 also has therapeutic potential in patients with stage III malignant melanoma and in patients with other solid cancers. If therapy is applied prior to the standard diagnostic sentinel lymph node biopsy (SLNB) or complete lymph node dissection (cLND), the prognosis for the patients may be improved as compared to surgical intervention alone. As described herein patients with stage III melanoma can be used to test and optimize the therapeutic potential of different immunomodulatory agents.

In certain embodiments of the present invention, the local s.c. injection is with about 1 cm of the location of the melanoma lesion. In other embodiments, the injection is from about 0 cm to about 5 cm from the location of the melanoma lesion. In certain embodiments, the s.c. injection is administered such that the IL-2 drains via the lymphatic vessels in the region of the melanoma lesion. In yet other embodiments, the IL-2 may be administered directly into the melanoma lesion or intra-dermally in close vicinity to the lesion. With the objective of targeting lymphatic drainage from the area of the primary lesion into the relevant tumor draining lymph nodes, some variability in injection site may be allowed, depending on the anatomical location in the body. Injection directly into the lymph nodes would also be possible, although less practical.

It is contemplated that the present invention is suitable for cancers beyond malignant melanoma. For such cancers, administration of the dose of IL-2 is made such that the IL-2 drains via the lymphatic vessels in the region of the cancerous lesion and the administration may be local to or directly into the area of the cancerous lesion.

When recombinant intereukin-2 is administered s.c. and locally at the site of a primary melanoma lesion, a fraction of the cytokine will drain via the lymphatic vessels to the draining lymph nodes allowing local high concentrations. The amount of an s.c. injected dose that drains to the lymphatic system is dependent on the molecular weight of the protein. IL-2 has a MW of approximately 15.000 KDa and expectedly around 40% of an injected dose should enter the lymphatic system. Porter C J H, Charman S A., *Lymphatic transport of proteins after subcutaneous administration*, J Pharm Sci 2000; 89(3):297-310; Chen S A, Sawchuk R J, Brundage R C et al., *Plasma and lymph pharmacokinetics of recombinant human interleukin-2 and polyethylene glycol-modified interleukin-2 in pigs*, J Pharmacol Exp Ther 2000; 293(1):248-259.

Figure 1:
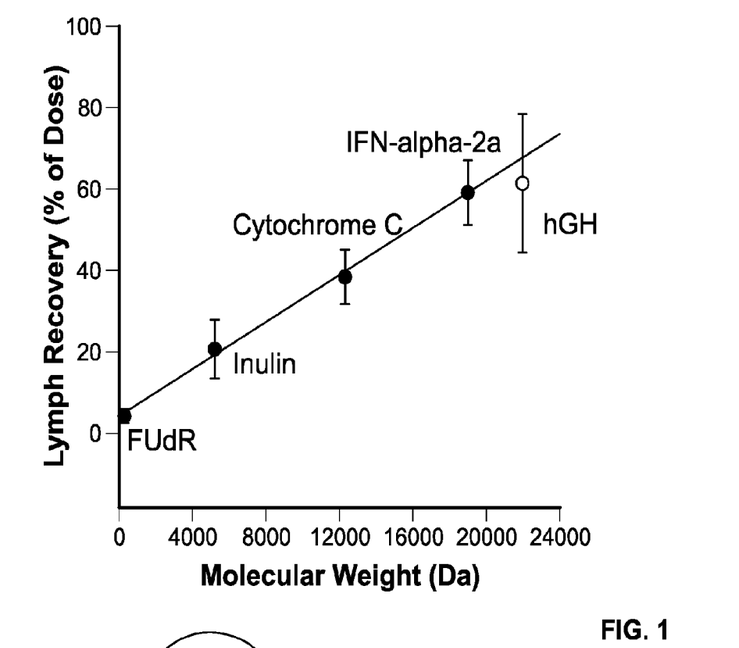
FIG. 1: Graph showing relationship between molecular weight and cumulative % dose recovered in popliteal lymph following s.c. administration into the lower part of the hind leg of sheep.
Figure 2:
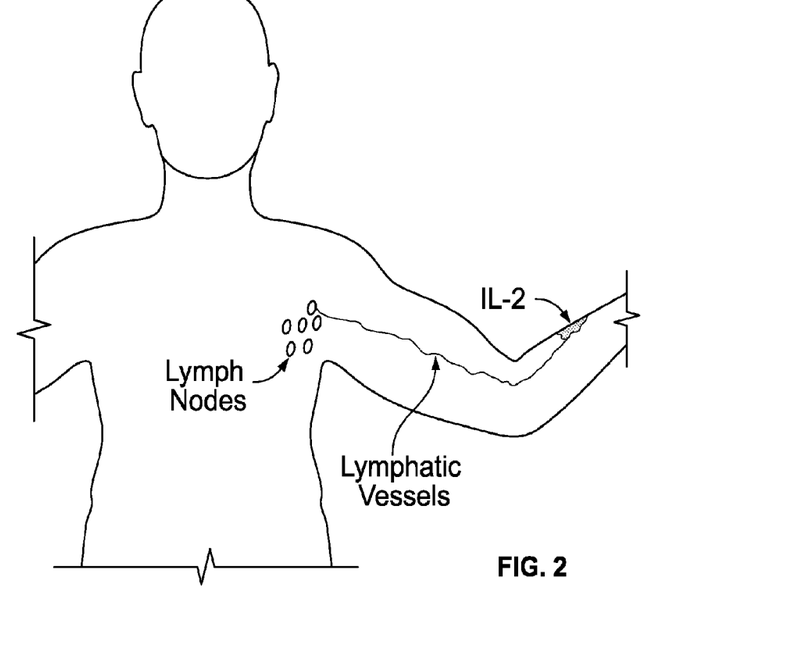
FIG. 2 is a schematic diagram of IL-2 injected locally in the area of the primary lesion and its subsequent drainage to the sentinel lymph node(s)

The relationship between molecular weight and cumulative % dose can be seen in the Figure below which shows recovered in popliteal lymph following s.c. administration into the lower part of the hind leg of sheep. Porter C J H, Charman S A., *Lymphatic transport of proteins after subcutaneous administration*. J Pharm Sci 2000; 89(3):297-310. (mean+/−SD, n=3-4). Data from Supersaxo et al. and Charman et al. The experience with lymphatic mapping (injecting radioactive dye) as used in the normal diagnostic SLN procedure directs that intradermal injection in the site where the primary lesion was biopsied or removed, relatively consistently will target the draining lymph nodes. Morton D L et Al. *Validation of the Accuracy of Intraoperative Lymphatic Mapping and Sentinel Lymphadenectomy for Early-Stage Melanoma*, Annals of Surgery, 1999; 230(4): 453-65. Subcutaneous administration of a cytokine would likely reach the same lymph nodes, based on the anatomical construct of the lymphatic system. For practical reasons s.c. administration would be preferred over intra-dermal administration and s.c. administration would still be considered relevant for targeting the relevant tumor draining lymph nodes.

Experiences with subcutaneous administration of IL-2 in pigs further supports that a fraction of the injected cytokine will drain into the lymphatic vessels. Chen S A, Sawchuk R J, Brundage R C et al., *Plasma and lymph pharmacokinetics of recombinant human interleukin-2 and polyethylene glycol-modified interleukin-2 in pigs*. J Pharmacol Exp Ther 2000; 293(1):248-259.

Within the draining lymph nodes, the normal immune response towards malignant cells has been suppressed by the presence of the primary lesion and potential metastatic seeds within the draining lymph nodes. That local immune suppression is ongoing in the tumour microenvironment and in the SLN has previously been described. Majewski T F, Meng Y, Harlin H., *Immune suppression in the tumor microenvironment*, J Immunother 2006; 29(3):233-240; Zou W., *Immunosuppressive networks in the tumour environment and their therapeutic relevance*. NAT REV CANCER 2005; 5(4):263-274. At ASCO 2007 data on TCRζ downregulation and Indoleamine 2,3-dioxygenase (IDO) upregulation in the SLN were presented (abstract 8000 by BP Negin, available at the virtual meeting for ASCO). IDO up-regulation locally has also been described (David Munn, discussion session, ASCO 2007). A local high concentration of IL-2 within the draining lymph nodes may revert the tumour induced tolerance towards the malignant cells within the sentinel nodes and potentially boost an antigen specific immune response towards also distant metastatic seeds. That a balance between immune surveillance and tumor progression is ongoing within the tumor draining lymph nodes (TDLNs) containing small metastatic deposits is also supported by the findings that malignant involvement of sufficiently small sizes (less than 0.1 mm) rarely leads to tumor relapse and is associated with high survival rate. van Akkooi A C, Nowecki Z I, Voit C, Schafer-Hesterberg G, Michej W, de Wilt J H, Rutkowski P, Verhoef C, Eggermont A M. *Sentinel node tumor burden according to the Rotterdam criteria is the most important prognostic factor for survival in melanoma patients: a multicenter study in* 388 *patients with positive sentinel nodes*. Ann Surg 2008 December; 248(6):949-55. This could be suggestive of the immune system being capable of clearing remaining smaller tumor deposits, once the immune suppressive primary lesion has been removed. Negin B, Panka D, Wang W, Siddiqui M, Tawa N, Mullen J, Tahan S, Mandato L, Polivy A, Mier J, Atkins M. *Effect of melanoma on immune function in the regional lymph node basin*. Clin Cancer Res 2008 Feb. 1; 14(3):654-9. In patients where slightly larger metastatic deposits are found, an exogenous immune stimulation could make the difference in shifting the balance towards reactivation of immune mediated anti-tumor responses. That local immune suppression to some extent may be reverted by IL-2 at relatively high local concentrations is supported by: Zippelius A, Batard P, Rubio-Godoy V et al., *Effector function of human tumor-specific CD8 T cells in melanoma lesions: a state of local functional tolerance.* Cancer Res 2004; 64(8):2865-2873; Yu P, Lee Y, Liu W et al. *Priming of naive T cells inside tumors leads to eradication of established tumors*, Nat Immunol 2004; 5(2):141-149. Munn D H et Al. *The tumor draining lymph node as an immune-privileged site*. Immunological Reviews 2006; 213: 146-58. Cochran A J, Tumour-induced immune modulation of sentinel lymph nodes. Nature Reviews, Immunology 2006; 6: 659-70.

Antigen presentation from the primary lesion has already taken place in the draining lymph nodes, but the expansion or activation of tumor associated antigen (TAA) specific T-cells has been suppressed. The biology of IL-2 predicts that a TAA specific T-cell response may be boosted with a relatively high local concentration of IL-2 in the lymph nodes draining the primary lesion. In a simple description, the normal function of the lymph node is to produce T- and B-cell responses to new or foreign antigens encountered in the periphery (following dendritic cell (DC)/antigen presenting cells (APC) presentation. That many patients at clinical presentation of melanoma have TAA specific T-cells circulating in peripheral blood indicates that antigen presentation and T-cell expansion has taken place to some extent. Zippelius A, Batard P, Rubio-Godoy V et al., *Effector function of human tumor-specific CD8 T cells in melanoma lesions: a state of local functional tolerance*. Cancer Res 2004; 64(8):2865-2873; If a 'T- and B-cell growth and maturation factor' like IL-2 was introduced at sufficiently high concentrations within the relevant lymph nodes, pre-existing but suboptimal T-cell expansion/activation could potentially be boosted providing in vivo expansion of relevant T-cells and B-cells. Some of these cells may then circulate and evoke anti-tumor responses towards distant metastatic seeds in the body.

This may ultimately result in improved survival for the patients compared to surgery alone, which is the standard therapy today.

Other cytokines/immuno-modulators may have similar therapeutic potential, if applied locally targeting immuno-modulatory relevant concentrations within the tumour draining lymph nodes. Relevant cytokines and immunomodulatory agents which could have similar effects includes, IL-2, IL-4, IL-15, IL-21, IL7 and IL-9. As previously mentioned, other cytokines like GM-CSF, G-CSF and Interferons like IFN-α, IFN-γ or other type 1 interferons would be expected to have some effect. Danger signals like CpG have shown immunomodulatory effects in the draining lymph nodes (see previously) and would also be expected to have some degree of therapeutic effect. Ultimately it would require in vivo testing of multiple immunomodulatory compounds or combinations of these administered over time to demonstrate which immunomodulatory intervention which would be most optimal.

Ultrasonograpy of the tumour draining lymph nodes and fine needle aspiration cytology to confirm presence of malignant cells within the draining lymph nodes is a technique which has been extensively explored by Dr. Christiane Voit at Charite, Berlin Germany. Published data shows that presence of malignant cells in the tumor-draining lymph nodes predict tumor involvement in the lymph nodes, when these lymph nodes are removed surgically. Voit C, Kron M, SchSfer G et al., *Ultrasound-guided Fine Needle Aspiration Cytology prior to Sentinel Lymph Node Biopsy in Melanoma Patients*. Ann Surg Oncol 2006; 13(12):1682-1689; Schaefer-Hesterberg G, Schoengen A, Sterry W, Voit C. *Use of ultrasound to early identify, diagnose and localize metastases in melanoma patients*, Expert Rev Anticancer Ther 2007; 7(12):1707-1716; van Akkooi A C J, Nowecki Z I, Voit C et al., *Sentinel Node Tumor Burden According to the Rotterdam Criteria Is the Most Important Prognostic Factor for Survival in Melanoma Patients A Multicenter Study in 388 Patients With Positive Sentinel Nodes*, Ann Surg 2008; 248(6):949-955; Voit C A, van Akkooi A C J, Schafer-Hesterberg G et al., *Rotterdam Criteria for Sentinel Node (SN) Tumor Burden and the Accuracy of Ultrasound (US)-Guided Fine-Needle Aspiration Cytology (FNAC): Can US-Guided FNAC Replace SN Staging in Patients With Melanoma?*, J Clin Oncol 2009; 27(30): 4994-5000; Voit C, van Akkooi A C J, Schafer-Hesterberg G et al., *Ultrasound Morphology Criteria Predict Metastatic Disease of the Sentinel Nodes in Patients With Melanoma*, J Clin Oncol. 2010; 28; 847-52; Voit C, Schoengen A, Schwurzer M, Weber L, Mayer T, Proebstle T M., *Detection of regional melanoma metastases by ultrasound B-scan, cytology or tyrosinase RT-PCR of fine-needle aspirates*, Br J Cancer 1999; 80(10):1672-1677. This technique enables to test the therapeutic potential of cytokines and other immunostimulatory agents in a clinical setting where patients are more responsive to immunotherapeutic interventions.

As most solid tumors initially spread via the lymphatic vessels, the therapeutic effect would also be present in other cancer indications including early stages of breast cancer, colon cancer, rectal cancer, prostate cancer, bladder cancer, head and neck cancer, lung cancer and cervix cancer.

The present invention uses unexpectedly low doses of IL-2 administered locally and neo-adjuvantly to patients with early stages of the disease. This will result in local high concentrations of IL-2 within the relevant tumour draining lymph nodes. Patients with only early stages of disease will be more responsive to immunotherapy resulting in improved survival of patients compared to current therapy standards. In certain embodiments, ultrasonograpy of the tumour draining lymph nodes and fine needle aspiration cytology will be used to verify presence of malignant cells within the draining lymph nodes before new-adjuvant treatment. In certain embodiments, the lymph nodes are removed at the completion of the neo-adjuvant treatment.

Certain embodiments of the present are performed using the technique of ultrasound guided fine-needle aspiration cytology for the testing of immunomodulatory agents effects on anti-tumour activity within the tumour draining lymph nodes. Patients which have been diagnosed with malignant melanoma based on a biopsy or removal of the primary lesion are usually scheduled to undergo sentinel lymph node biopsy (SLNB). In connection with this procedure patients will undergo lymphatic mapping with injection of radioactive, blue colloid in order to locate the relevant sentinel lymph nodes. Based on the lymphatic mapping, patients will then be examined by ultrasonography and in case the ultrasonography indicates presence of malignant cells, a fine needle biopsy will be performed to verify the presence of malignant cells. In patients with malignant cells in the lymph nodes the testing of IL-2 or another immunomodulatory compound can be initiated.

In certain embodiments, during the neo-adjuvant treatment period, the regional lymph nodes are assessed by weekly ultrasound. At the end of the neo-adjuvant treatment period, the patient undergoes SLNB or complete lymph node dissection including the sentinel lymph nodes, which are identified by repeated lymphatic mapping. The lymph nodes will undergo extensive slicing. A histological examination may be conducted involving immune histochemical staining with markers such as Melan-A and HMB-45 will be conducted to determine signs of micro- or macro-metastatic disease.

When reviewing the package inserts for Proleukin® from US, Germany and Denmark, it is clear that different doses and regimens and routes of administration (i.v. and s.c.) are being recommended.

The highest doses are recommended in the U.S. labeling which calls for approximately 7.7 mg per day during dosing (600.000 IU/kg every 8 hours) and a total of approximately 72.5 mg over a full treatment course of 4 weeks. (under the assumptions of a person weighing 70 kg and being 1.80 m of height).

Intravenous doses in the German and Danish package inserts result in approximately 2 mg per day and a total of approximately 41.4 mg administered i.v. over a period of 7 weeks.

The Danish package insert also provides recommendations for subcutaneous administration. Here the doses provide for a maximum of approximately 1.1 mg per day and results in a total of approximately 23.1 mg being administered s.c. over a period of 10 weeks.

Table 1 provides an overview of doses according to label and the doses which according the invention described herein would be effective:

Calculation:
600.000 IU/kg i.v. every 8 hours (15 min infusion) for 5 days total 14 doses—times 2 separated by 2 weeks. Person weighing 70 kg:
(0.6 million IU/kg*70 kg*14 doses=588 MIU over 5 days—times 2=1076 MIU)
or
(0.037 mg/kg*70 kg*14=36.26 mg over 5 days—times 2=72.5 mg)
(Dose per 24 hours during cycle is 126 million IU (7.7 mg))
The U.S. package insert further informs that:
Proleukin® biological potency is determined by a lymphocyte proliferation bioassay and is expressed in International Units (IU) as established by the World Heath Organization $1^{st}$ International Standard for Interleukin-2 (human). The relationship between potency and protein mass is as follows: 18 million ($18\times10^6$) IU Proleukin®=1.1 mg protein The German package insert calls for a dose of 18 million IU/m² body surface area, administered IV over a period of 24 hours as a continuous infusion. The dose is repeated every day, for 5 days, followed by 2-6 days of rest before another 5 days of continuous dosing is repeated, followed by a further 3 weeks of rest. This represents an induction cycle. Two induction cycles are administered as individually tolerated.
Calculation:
18 million IU*1.88 m2=33.84 million IU per day (=2.068 mg per day) times 5 days

TABLE 1

Doses of IL-2 according to label text and as local neo-adjuvant treatment

| | i.v. administration | | s.c. administration | |
|---|---|---|---|---|
| | Full treatment | | | |
| | course/ duration | Max daily dose | Full treatment course /duration | Max daily dose |
| US label | 72.5 mg/4 weeks | 7.7 mg | N/A | N/A |
| German label | 41.4 mg/7 weeks | 2 mg | N/A | N/A |
| Danish label | 41.4 mg/7 weeks | 2 mg | 23.1 mg/10 weeks | 1.1 mg |
| Optimal neoadjuvant administration | N/A | N/A | 12 µg (0.012 mg) | 1 µg (1000 ng) (0.001 mg) |
| Range for neoadjuvant administration | | | 120 ng – 2.4 mg [00054] (0.000012 – 2.4 mg) | 10 ng – 200 µg (0.000001 – 0.2 mg) |
| Radny et Al - intra-lesional in stage IV pts. | | | 0.44 – 4.4 mg | 0.037 – 0.37 mg |

According to the U.S. package insert, the recommended Proleukin® for injection treatment regimen is administered by a 15-minute IV infusion every 8 hours. Each course of treatment consists of two 5-day treatment cycles separated by a rest period. The insert calls for 600,000 IU/kg (0.037 mg/kg) dose administered every 8 hours by a 15 minute IV infusion for a maximum of 14 doses. Following 9 days of rest, the schedule is repeated for another 14 doses, for a maximum of 28 doses per course, as tolerated. During clinical trials, doses were frequently withheld for toxicity. Metastatic RCC patients treated with this schedule received a median of 20 of the 28 doses during the first course of therapy. Metastatic melanoma patients received a median of 18 doses during the first course of therapy, according to label.

33.84*5 days*2=338.4 million IU (20.68 mg) administered over 12-16 days.
When this is repeated after 3 weeks of rest, the total dose is 676.8 million IU or 41.36 mg administered IV over a period of 7 weeks.

The Danish product summary describes both an IV and a subcutaneous administration. The dose for the continuous IV infusion is 18 million IU/m² body surface area, administered IV over a period of 24 hours as a continuous infusion. This dose is repeated every day, for 5 days, followed by 2-6 days of rest before another 5 days of continuous dosing is repeated, followed by a further 3 weeks of rest. This represents an induction cycle. Two induction cycles are administered as individually tolerated.

A maintenance dose is also described for individuals who respond to therapy, with up to four maintenance infusions administered. The suggested maintenance dose is 18 million IU administered over 5 days and repeated with a 4 weeks pause in between each infusion.

The dose for Subcutaneous administration (s.c.) is:
Week 1: 18 million IU every day for 5 days followed by 2 days of rest.
Week 2-4: 18 million IU on days 1 and 2 of each week and 9 million IU on days 3, 4 and 5.
No drug is administered on days 6 and 7 of each week.
Week 5: no treatment is administered
Weeks 6-10: Treatment is repeated as given in weeks 1-4.

An s.c. maintenance dose is described for individuals who respond to therapy, maintenance regimens as indicated above can be administered.

Calculation:
Doses for continuous i.v. administration are the same as from the German package insert. See above, i.e.: the total dose is 676.8 million IU or 41.4 mg administered IV over a period of 7 weeks.
The maintenance regimen would result in an additional 4*18 million IU=72 million IU or 4.4 mg administered over a period of 20 weeks
The subcutaneous regimen would provide:
Week 1: 5*18 MIU=90 million IU (5.5 mg)
Weeks 2-4: 18+18+9+9+9=63 million IU (3.85 mg) per week times 3 weeks=189 million IU (11.55 mg)
In a 10 week period a total of 378 million IU (23.1 mg) would be administered Often a dose of 25 ng/ml of IL-2 is used for in vitro experiments. Effective doses of IL-2 in vitro would be considered to be in the range 1 U/ml (0.061 ng/ml) to 1000 U/ml (61 ng/ml), although higher doses would also have activity.

Montes et al 2005 purportedly applies three doses of IL-2: 10 U/ml (low dose, 0.61 ng/ml), 100 U/ml (6.1 ng/ml) and 1000 U/ml (high dose, 61 ng/ml) for in vitro CD8+ T-cell expansion. Montes M et Al. Optimum in vitro expansion of human antigen-specific CD8+ T cells for adoptive transfer therapy. Clinical and Experimental Immunology 2005; 142: 292-302. The dose response observed with the highest doses resulted in the largest degree of T-cell expansions.

The present invention contemplates a lower dose of IL-2 than used in the prior art, such that effective doses reach the sentinel node (i.e. the tumor draining lymph node) after sub cutaneous administration, with decreased occurrence of serious side effects seen in the higher dose administration.

Once T-cells and B-cells are stimulated with IL-2 within the lymph nodes it would be expected that also autocrine production of IL-2 and other cytokines would contribute to the local concentration of IL-2 (and other cytokines) within the lymph node. This would expectedly result in proliferation and maturation of T-cells and B-cells.

This stimulation of the T-cells and B-cells within the tumor draining lymph nodes will result in a reversion of the state of immune suppression exerted by the primary lesion and possible local presence of tumor cells. Clonal expansion and maturation of relevant antigen specific cells will result in anti-tumor responses to tumor cells located within the tumor draining lymph nodes, to tumor cells located in the area of the primary lesion (partly via cell coded homing to the area of the primary lesion) and tumor cells having spread to distant parts of the body (metastatic seeds).

Figure 3:
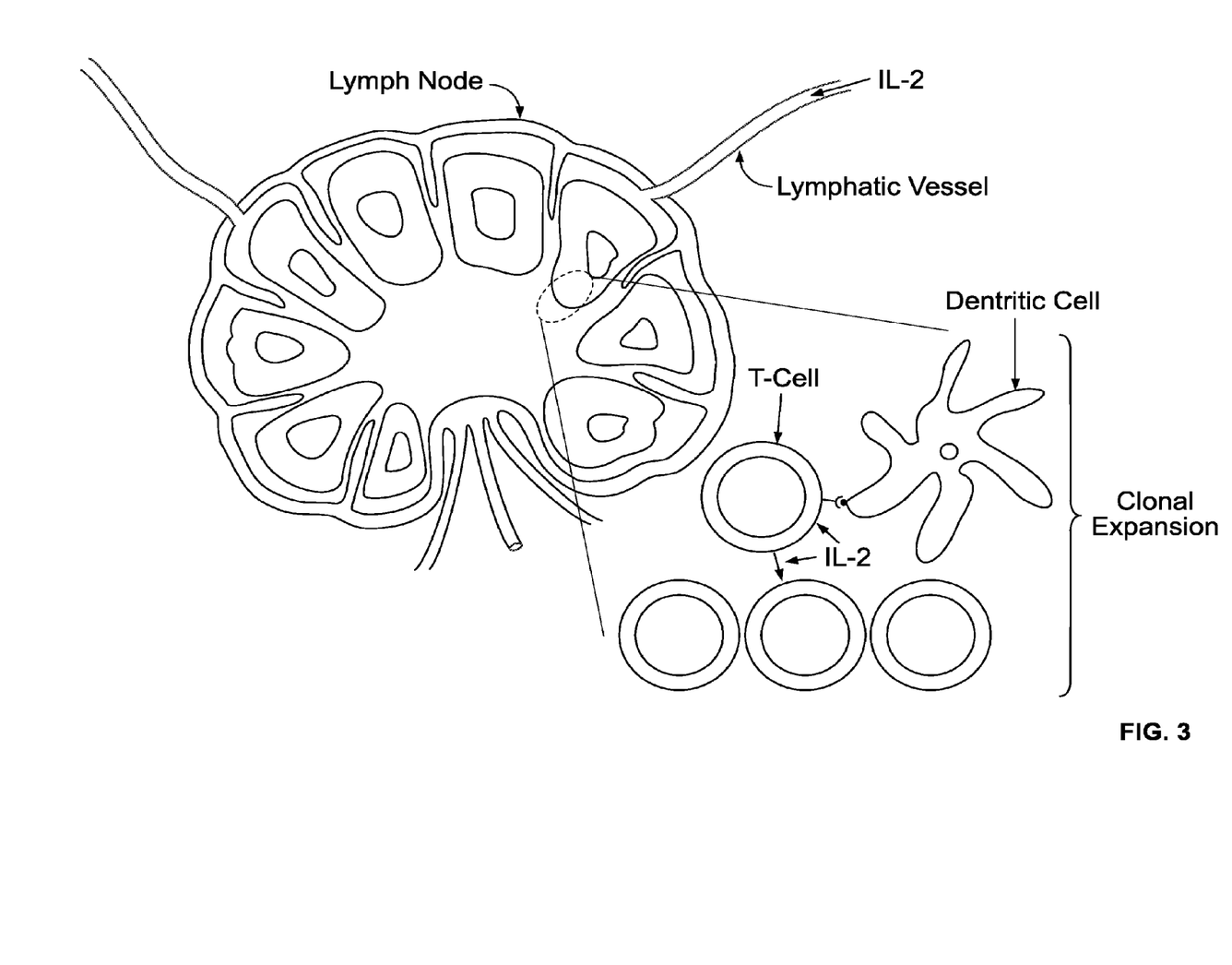
FIG. 3 is a schematic diagram of IL-2 reaching a sentinel lymph node/tumor draining lymph node and magnification of cell interactions (including antigen presenting cells (eg. dendritic cells (DC)) stimulating antigen specific T-cells) and stimulation with local high concentrations of IL-2 leading to clonal expansion of antigen specific cells
Figure 4:
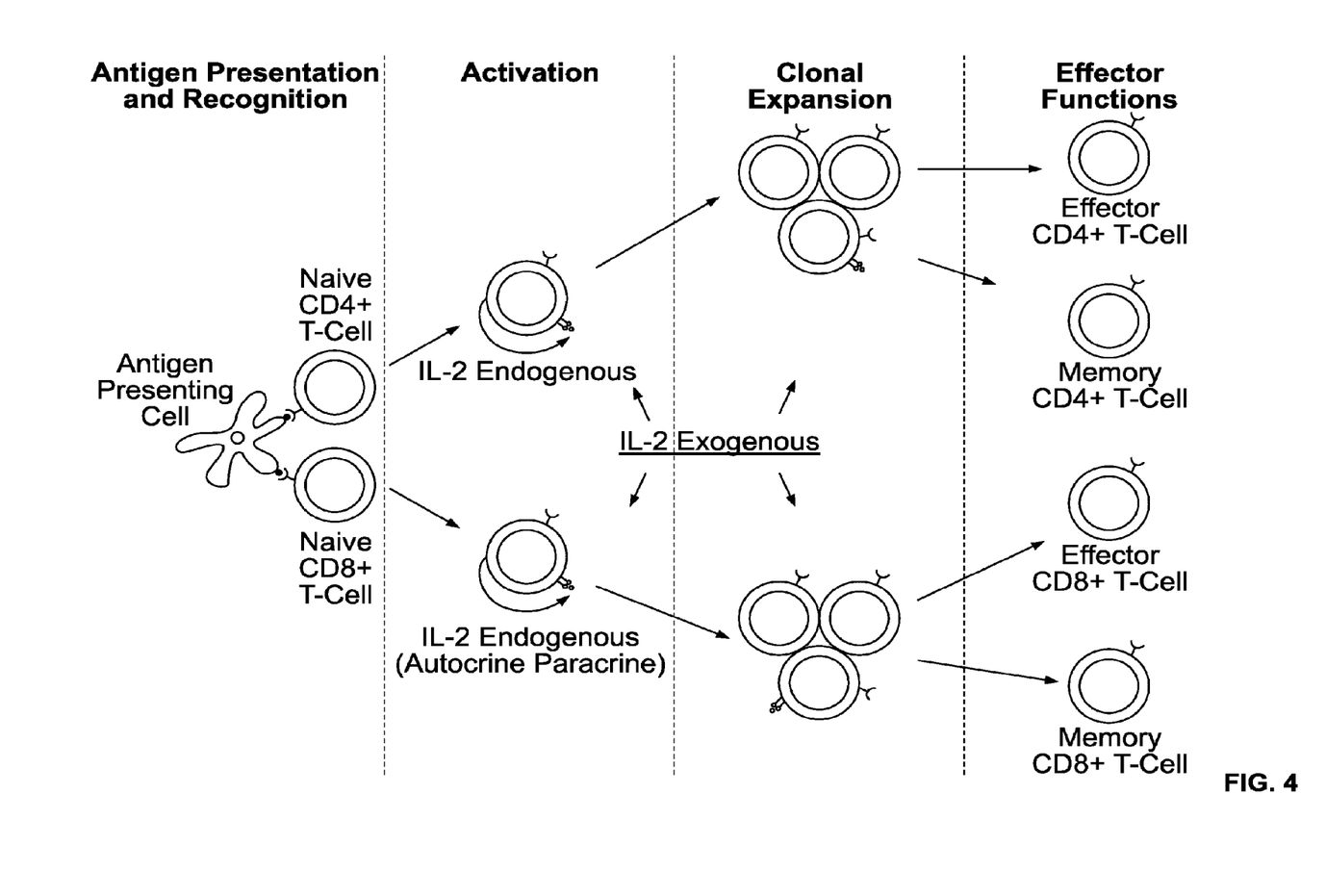
FIG. 4 is a schematic diagram of antigen presentation and recognition by antigen specific T-cells, activation by endogenous produced and exogenous administered IL-2, clonal expansion of antigen specific T-cells and maturation into CD4+ and CD8+ effector and memory T-cells
Figure 5:
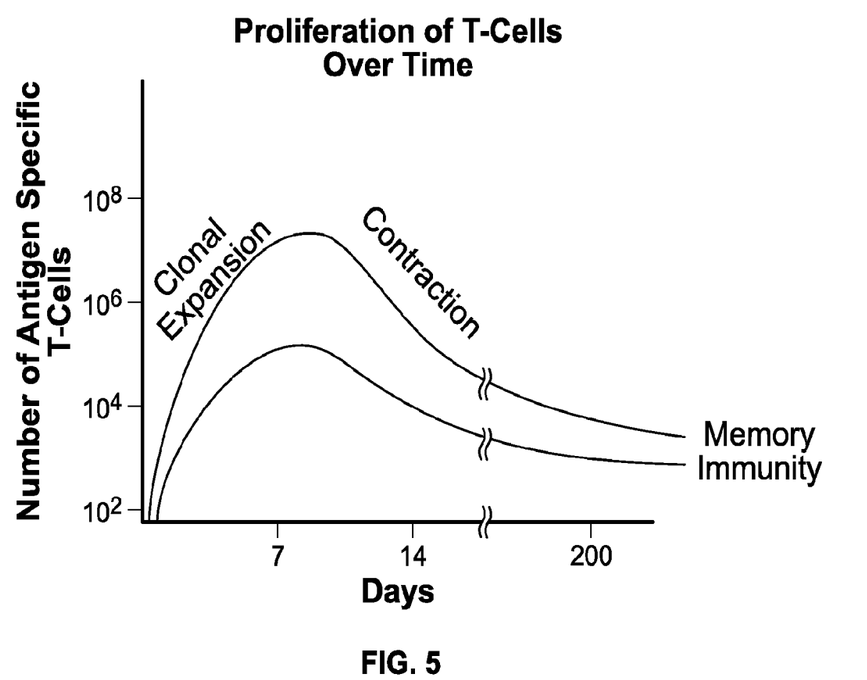
FIG. 5 is a graph showing the time course of clonal T-cell expansion and subsequent contraction following a normal effective antigen specific T-cell stimulation (CD8+, upper line and CD4+, lower line)

FIG. 3 illustrates the process of activation, proliferation and maturation which may be stimulated by exogenous administered IL-2.

Sufficient activation of antigen specific T-cells will result in autocrine production of IL-2 (and other cytokines) which will stimulate the T-cell and other T-cells in the microenvironment to express the high affinity IL-2 receptor (IL-2R$\alpha\beta\gamma$) and stimulation with IL-2 via this receptor will further stimulate proliferation and maturation.

The time needed to generate effective numbers of activated T helper cells (CD4+) and cytotoxic T-cells (CD8+) with antigen specificity is usually approximately 4-14 days.

The lymph node is essentially a T- and B-cell factory which can ensure presentation of relevant antigens and facilitate clonal expansion of the relevant T- and B-cells possessing specificity towards the relevant antigens. IL-2 is important in both clonal expansion and maturing the cells into effector cells.

Within the tumor draining lymph node, tumor antigens have already been presented but clonal expansion is being suppressed by the primary cancer lesion and possibly also the microenvironment, which may also contain tumor deposits. By local administration of IL-2, or a similar relevant stimulatory and proliferation signal, it is hypothesized that local immuno-suppression may be reverted and clonal expansion of relevant T- and B-cells can be achieved. This would expectedly result in local anti-tumor immune responses and likely also anti-tumor responses towards the primary lesion and small metastatic deposits other places in the body. The key is to administer IL-2 early in the course of the disease, ie. before the cancer cells have become clonally very diversified and has established themselves in a microenvironment which allows immune escape.

Dosing:
The neo-adjuvant IL-2 treatment of the present invention will be administered with the objective of reaching local concentrations within the tumor draining lymph nodes of about 1 ng/ml to about 250 ng/ml or more. For treatment of melanoma, this dose can be administered by a number of s.c. injections in the local region of the melanoma spaced out over a treatment period of from about 1 to about 8 weeks. The IL-2 may be given daily, weekly or a number of times over the course of week. Preferably, the dosing involves a resting period of one or more days in between administration of IL-2 injection. This would allow the microenvironment within the draining lymph nodes to return towards more normal states and allow signaling via other cytokines in the microenvironment.

Low Dose Embodiment
In one embodiment of the present invention, a very low dose of IL-2 is administered such that a total dose of about 10 to about 1000 ng is locally administered in the area of the primary lesion via s.c. injection over about 4 weeks.

The present invention incorporates effective doses for a local and neo-adjuvant setting targeting local high concentrations of IL-2 in the sentinel (tumor draining) lymph nodes, with minimal systemic side effects.

In one embodiment of the present invention, a very low dose of IL-2 is administered such that a total dose of about 10 to about 1000 ng is locally administered via s.c. injection neo-adjuvantly. In certain embodiments, neo-adjuvant treatment extends over a 4 weeks period of time. Treatment durations in the range of about 1 to 8 weeks would be considered effective depending on the specific clinical setting. In vitro doses as low as 1 ng/ml may be effective locally within the tumor draining lymph nodes. Furthermore, once the T-cells and B-cells have been stimulated within the tumor draining lymph nodes, autocrine production and stimulation will come in effect and provide the necessary immune response.

In order to cover the dose-range which would be considered therapeutically relevant, a low dose and a high dose calculation will be provided, including the assumptions behind the dose calculations. Furthermore, an optimal dose will be proposed including the assumptions behind this. It is important to understand that although higher doses would be considered to have therapeutic effect, the minimum effective doses would be much lower than the product labels indicate and would likely be associated with less side effects.

Low Dose Scenario:

Concentrations as low as 1 ng/ml within the draining lymph nodes may be effective. Once the T-cells and B-cells have been stimulated within the tumor draining lymph nodes, autocrine production and stimulation of IL-2 and other cytokines will come in effect and provide the necessary immune response.

Calculation of required dose aiming at concentrations of 1-10 ng/ml within the draining lymph nodes: Assuming that the injected dose would be diluted in eg. 10 ml of lymph, the required dose would be 10-100 ng of IL-2 injected in a volume of eg. 0.2 to 1.0 ml. at the site of the primary lesion.

High Dose Scenario:

In order to stimulate the microenvironment within the draining lymph nodes over more extended periods of time higher doses would be required. Assuming that only 40% of an injected dose will drain via the lymphatic vessels to the relevant lymph nodes (see above) and that the half life (T½) of IL-2 within the lymphatic vessels is relatively short, at about 30-60 minutes, somewhat higher doses could be desirable. It will likely take about 30 min for the injected dose of cytokine to reach the lymph nodes but depending on the anatomical location of the primary lesion, this could take up to 2-3 hours for the injected dose to reach the lymph nodes. The injected dose would again be diluted in approximately 10 ml of lymph and it will take approximately 12 more hours before the injected dose has been washed away from the injection site.

Furthermore, in some cases the pressure within the tissue has been increased due to the rapidly expanding tumor cell mass within the capsule of the lymph node and this requires higher doses of IL-2 to penetrate the tissue structures.

Calculations for Required Dose, Example:

40% of 200 µg (3.27 million IU) will drain via the lymph (=0.08 mg) and dilutes in approx. 10 ml of lymph. The average resulting concentration in lymph after dilution of 0.08 mg/10 ml=0.008 mg/ml=8 µg/ml=8000 ng/ml.

Assuming that drainage would be relatively slow and tissue pressure could delay lymph flow, it could take 2-3 hours for the injected dose to reach the lymph node.

At 2 hours, given a half life of 30-60 min, the concentration in the lymph reaching the nodes will be in the range 8000 ng/ml/$2^4$ to 8000 ng/ml/$2^2$=500-2000 ng/ml.

At 6 hours the concentration will be in the range 8000/$2^{12}$ to 8000/$2^6$=1.95 ng/ml (if T½ is 30 min) to 125 ng/ml (if T½ is 60 min)

At 13 hours the concentration will be below 1 ng/ml if T½ is 60 min, ie. below biologic activity level. However, endogenous production of IL-2 and other cytokines would likely contribute to continued immune activation.

Consequently, under these assumptions there should be effective stimulation within the lymph node in the time period from 2 hours and up to at least 6-12 hours depending on the half life of IL-2 within the lymphatic vessels.

Even high doses would be likely to have therapeutic effect, but also be associated with more side effects.

Optimal Dose Selection:

After injection of 1000 ng (16,360 IU) IL-2 in a volume of eg. 0.6 ml, lymphatic drainage towards the tumor draining lymph nodes will start. Initially, the injected volume will spread out in the tissue covering an about 1- about 2 $cm^2$ area under the skin. Approximately 30% of the injected volume (300 ng) will enter the lymphatic vessels immediately and start traveling towards the tumor draining lymph nodes. About 30 minutes later, the first portion of the injected IL-2 will enter the lymph node and given an assumed half life ($T_{1/2}$) of 30 min on IL-2, the concentration at 30 minutes post injection will be approximately 100 ng/ml (taking into account dilution with lymph form other areas which the lymph node drains. This concentration will be 4-20 fold higher than what would be needed to stimulate IL-2 responsive cells.

Approximately 10% of the injected dose will enter the blood stream within the first hour—and thereby not enter the lymphatic vessels.

The next 20% of the injected dose (200 ng) will be washed slowly into the draining lymph node over a period of 30 min to 2 hours and will result in a concentration of IL-2 within the lymph node in the range of from about 12.5 to about 100 ng/ml at 1 to 3 hours post injection. This concentration would still be considered biologically active.

At 4 to about 6 hours post injection, concentrations of IL-2 will start to go below about 5 ng/ml and thereafter below the threshold for biologic activity. It is likely that autocrine production of IL-2 and other cytokines could now contribute and maintain cell stimulation in the period 8-24 hours.

In certain embodiments of the present invention a sufficiently high dose is used such that a concentration of about 1 to about 250 ng/ml locally within the draining lymph nodes are achieved (effective concentration in vitro 5-25 ng/ml) is locally administered via s.c. injection neo-adjuvantly. In certain embodiments, neo-adjuvant treatment with intermittent dose administrations extending over a period of about 4 weeks is applied.

Radny et al, showed that doses of 0.6 million IU to 6 million IU were effective in treating skin and soft tissue metastases from malignant melanoma when administered intra-lesionally to patients with stage III or IV melanoma having single or multiple skin and soft-tissue metastases as part of the clinical presentation of their disease. A total of 209 out of 245 lesions treated disappeared completely in this trial and demonstrates an impressive local response with locally high concentrations of IL-2.

From Radny, 2003:

TABLE 3

Treatment regimen

| Lesion size maxim, diameter (mm) | Single dose MIU | Stock solution (ml) | Duration of treatment (weeks) |
| --- | --- | --- | --- |
| <5 | 0.6 | 0.2 | 2 |
| >5 | 1.2 | 0.4 | 3 |
| >10 | 3.0 | 1.0 | 4 |
| >20 | 6.0 | 2.0 | 4 |

British journal of Cancer (2003) 89(9), 1620-1626

The present invention builds on this knowledge, but adds several important steps in combination to optimize the therapeutic effects. Firstly, patients with stage IV disease are not ideal for immunotherapeutic interventions. Patients with early stages of disease will be more likely to respond and prior removal of the primary lesion will reduce the immunosupressive effects of the tumour on the microenvironment within the lymph nodes. The malignant cells are less clonally diversified and have not yet developed multiple effective ways of escaping an immune attack. Subsequent removal of the tumor draining lymph nodes may further enhance the therapeutic benefit for patients as remaining tumor cells may be removed while tumor reactive T cells and B cells remain in the body.

In view of the above, the present invention contemplates lower doses of IL-2 than would previously have been thought effective, even in the setting tested by Radny et al. The present invention allows for relatively low doses of IL-2 to be applied in patients with the objective of reaching high local concentrations within the draining lymph nodes. In such patients anti-tumor responses to yet undetected metastatic seeds may also be considered possible.

The neo-adjuvant treatment period should not be less than 1-2 weeks in order to allow for effective clonal expansion of the T-cells (4-14 days). The total treatment period may extend for up to 8 weeks. In certain embodiments, a 4 week treatment is used.

In order to stimulate the immune system effectively, doses should be repeated. Weekly dosing would be the minimum dosing frequency in order to fulfill this objective. The local immune system is allowed to recover and normalize the cytokine microenvironment to some extent between doses applied. It is expected that continuous dosing would be less effective than intermittent dosing. In certain embodiments, dosing will be administered on a thrice weekly basis to allow for this normalization between dosing.

In an embodiment of the present invention, low doses are administered on a daily basis or over a 5 days interval of daily dosing followed by a resting period of eg. a week before another 5 days of dosing would be applied. For example a. 5+9 regimen may be instituted which would be repeated eg. twice (5 days of dosing followed by 9 days of rest, repeated eg. two times).

When the first tumor cells are killed following the stimulated immune attack, new tumor specific antigens may be presented to which new antigen specific T-cells will have specificity. Consequently, immune stimulation over at least a few weeks would be preferred to make the immune response as effective as possible.

For example, a fixed total dose of 1000 ng (16,360 IU) of IL-2 is administered in a volume of eg. 0.6 ml in a thrice weekly regimen for a period of 4 weeks. In another embodiment a fixed total dose of 10-100 ng (163.6-1636 IU) of IL-2 injected in a volume of eg. 0.2 to 1.0 ml is administered. In certain embodiments, this dose is administered over a four week period in a thrice weekly regimen. In a further embodiment, 200 µg (3.27 million IU) injected in a volume of eg. 0.2 to 1.0 ml is administered. In certain embodiments, this dose is administered over a four week period in a thrice weekly regimen.

In embodiments having daily doses of about 1000 ng of IL-2 administered s.c. to a patient, the dose is about 1000 to about 7700 times lower than recommended systemic induction doses, according to labeling. It would be about 36 to about 360 times lower than the doses applied by Radny et al. Doses of about 200 µg would be similar to the doses used by Radny et Al., but administered to a different patient population.

Total and accumulated induction therapy doses applied in the 'optimal scenario' would be 1925-6041 times lower than recommended systemic induction doses, according to labeling (23.1 mg/12 µg=1925 and 72.5 mg/12 µg=6041, respectively (see table 1 for reference).

The IL-2 may be administered by local administration in the area of the primary lesion. For melanoma, this could be within about 1 cm of the primary lesion, but could be 0-5 cm away from the primary lesion, depending on the anatomical location of the primary lesion. For melanoma, IL-2 could be injected subcutaneously or intradermally in the area of the primary lesion, in a location which has the same draining lymph node or directly into the sentinel lymph node(s)/tumor draining lymph node(s).

EXAMPLES

Example I

Patients with stage III melanoma as identified by high-resolution ultrasonography and fine needle aspiration cytology (FNAC) will be treated. Prior to ultrasonography, the diagnosis of melanoma will have been made based on removal of a skin lesion showing malignant melanoma cells by histology. Patients will receive recombinant IL-2 administered s.c. in the area of the primary lesion for 4 weeks in a thrice weekly regimen prior to complete regional lymph node dissection. In one embodiment, the dose applied will be about 110000 ng of IL-2 (110 µs or 1.8 million IU) per dose administration. In other embodiments, even lower doses would be effective. In certain embodiments, the doses will be about 1000 ng per dose administration resulting in a total dose of 12 µg of IL-2 administered over a period of 4 weeks using a thrice weekly dosing schedule.

After completion of the 4 weeks of local neo-adjuvant IL-2 therapy the patient may undergo complete regional lymph node dissection. The lymph nodes will be examined by extensive slicing and histological examination involving immune histochemical staining with Melan-A and HMB-45 to establish whether signs of micro- or macro-metastatic disease can be observed. It is hypothesized that treatment with IL-2 administered neo-adjuvantly prior to lymph node removal will result in anti-tumor activity locally and improve survival for patients relative to surgery alone.

Example II

Patients with stage I-II melanoma, as identified by a biopsy or surgical removal of the primary lesion, showing malignant melanoma cells by histology, would be treated. Patients will receive recombinant IL-2 administered s.c. in the area of the primary lesion for 4 weeks in a thrice weekly regimen prior to SLNB or complete regional lymph node dissection. The dose applied will be about 100-10000 ng per injection. Based on theoretical considerations on lymphatic drainage, an optimal dose would be about 1000 ng per dose administration resulting in a total dose of 12 µg of IL-2 administered over a period of 4 weeks using the thrice weekly dosing schedule. Depending on the location of the primary lesion, the patient may be able to self administer the doses of IL-2.

After completion of the 4 weeks of local neo-adjuvant IL-2 therapy the patient may undergo biopsy of the sentinel node(s) or in some cases complete regional lymph node dissection, as considered appropriate by the treating physician. The lymph nodes will be examined by extensive slicing and histological examination involving immune histochemical staining with markers for tumor cells such as Melan-A and HMB-45 to establish whether signs of micro- or macro-metastatic disease can be observed. It is hypothesized that treatment with IL-2 administered neo-adjuvantly prior to lymph node removal will improve survival for patients relative to current practise involving surgery alone.

Example III

Patients with breast cancer treated with insertion of a catheter after surgical removal of the primary lesion and subsequent local administrations of IL-2 for a period of about 4 weeks prior to the possible removal of sentinel lymph node(s) or cLND.

Example IV

Patients with early stages of cervical cancer or precancerous lesions treated with local administrations of IL-2 injected into the cervix. This therapeutic intervention would likely have therapeutic benefit if administered prior to or after eg. conisation.

What is claimed:

1. A method for treating a cancer selected from the group consisting of malignant melanoma and breast cancer, comprising:
    administering to a patient of a neo-adjuvant dose of from about 10 ng (164 IU) to about 200 µg (16364 IU) of IL-2 locally in an area of a primary tumor or in a location which drains to tumor draining lymph nodes to stimulate an immune response in the tumor draining lymph nodes; and
    surgically removing the lymph nodes after stimulation of the immune response by the tumor draining lymph nodes.

2. The method of claim 1, wherein the cancer is early stage malignant melanoma (eg. high risk stage I or stage II according to the American Joint Committee on Cancer classification (eg. version 2006).

3. The method of claim 2, wherein the malignant melanoma is stage I-III according to AJCC.

4. The method of claim 1, wherein said dose is from about 100 to about 1000 ng.

5. The method of claim 1, wherein the dose of IL-2 is administered subcutaneously or intradermally.

6. The method of claim 1, wherein the IL-2 is administered thrice weekly for about a four week period of time.

7. The method of claim 1, wherein the IL-2 is administered intermittently with about 5 days of dose administrations following a resting period for about 9 days, after which the patient is treated for about another 5 day period of time and rested for about 9 days before possible removal of the tumor draining lymph nodes.

8. The method of claim 1, wherein the primary tumor has been removed or malignant cells of the primary tumor have been destroyed such that the immunosuppressive effects of the primary lesion on the tumor draining lymph nodes has been reduced.

9. The method of claim 1, wherein the cancer is an early stage of breast cancer or maligant melanoma, wherein the IL-2 is administered either by continuous infusion into the area of the primary tumor or by intermittent administrations by injection.

10. A method of claim 1, wherein the dose is administered about 1 cm or less away from the primary tumor.

11. A method for treating a cancer selected from the group consisting of malignant melanoma and breast cancer, comprising:
    administering to a patient a neo-adjuvant dose of from about 10 ng (164 IU) to about 200 µg (16364 IU) of IL-2 directly into the area of a primary tumor to stimulate an immune response towards cancer cells;
    removing the primary tumor prior to initiation of administration of IL-2 or at about the same time as initiation of the administration of IL-2;
    surgically removing the lymph nodes after the immune response to the cancer cells has been stimulated.

* * * * *